(12) United States Patent
Nadim

(10) Patent No.: US 10,575,843 B2
(45) Date of Patent: Mar. 3, 2020

(54) KNOTLESS SUTURE ANCHOR

(71) Applicant: Ring Orthopedics, Inc., Tampa, FL (US)

(72) Inventor: Yasser Nadim, Somerset, KY (US)

(73) Assignee: Ring Orthopedics, Inc., Tampa, FL (US)

( * ) Notice: Subject to any disclaimer, the term of this patent is extended or adjusted under 35 U.S.C. 154(b) by 154 days.

(21) Appl. No.: 15/980,840

(22) Filed: May 16, 2018

(65) Prior Publication Data
US 2019/0216455 A1 Jul. 18, 2019

Related U.S. Application Data

(60) Provisional application No. 62/618,465, filed on Jan. 17, 2018.

(51) Int. Cl.
*A61B 17/04* (2006.01)

(52) U.S. Cl.
CPC .... *A61B 17/0401* (2013.01); *A61B 2017/044* (2013.01); *A61B 2017/0409* (2013.01); *A61B 2017/0414* (2013.01); *A61B 2017/0445* (2013.01); *A61B 2017/0459* (2013.01); *A61B 2017/0464* (2013.01)

(58) Field of Classification Search
CPC ........ A61B 17/0401; A61B 2017/0409; A61B 2017/0414; A61B 2017/044; A61B 2017/0445; A61B 2017/0459; A61B 2017/0464
See application file for complete search history.

(56) References Cited

U.S. PATENT DOCUMENTS

| | | | |
|---|---|---|---|
| 7,494,496 B2* | 2/2009 | Swain | A61B 17/0401 606/151 |
| 7,837,710 B2* | 11/2010 | Lombardo | A61B 17/0401 606/232 |
| 8,162,978 B2 | 4/2012 | Lombardo et al. | |
| 8,535,350 B2 | 9/2013 | Lizardi et al. | |
| 8,613,756 B2 | 12/2013 | Lizardi et al. | |
| 9,364,210 B2 | 6/2016 | Gregoire et al. | |
| 9,414,834 B2* | 8/2016 | Palese | A61B 17/0401 |
| 9,451,942 B2 | 9/2016 | van der Burg et al. | |
| 9,566,058 B2 | 2/2017 | Anspach, III et al. | |

(Continued)

*Primary Examiner* — Darwin P Erezo
*Assistant Examiner* — Alexis D Amechi
(74) *Attorney, Agent, or Firm* — Larson & Larson, P.A.; Justin P. Miller; Frank Liebenow

(57) ABSTRACT

A suture anchor for deployment in a preformed bone hole to secure soft tissue to bone. The anchor includes a proximal part, a distal part, an inner tube part and a ring part. The ring part is configured to move independently relative to the proximal part, inner tube part and distal part and further comprises two pairs of opposing apertures defining two suture passageways between an outer surface of the inner tube part and inner surface of the ring part. Before or after being connected to soft tissue, a suture is directed through the two suture passageways. Tension on the tissue can be adjusted by maneuvering the suture in the ring part without interfering with advancement of the distal part into the bone. The anchor has a center bore extending longitudinally between a distal end and proximal end of the anchor and is configured to receive an insertion guide.

10 Claims, 17 Drawing Sheets

(56) References Cited

U.S. PATENT DOCUMENTS

| | | |
|---|---|---|
| 2006/0106422 A1* | 5/2006 | Del Rio .............. A61B 17/0401 |
| | | 606/232 |
| 2016/0310128 A1 | 10/2016 | Denham |
| 2017/0172560 A1 | 6/2017 | Patel et al. |
| 2017/0231617 A1 | 8/2017 | Levinsohn |
| 2017/0231620 A1 | 8/2017 | Vijay et al. |
| 2018/0185019 A1* | 7/2018 | Lunn .................. A61B 17/0401 |

* cited by examiner

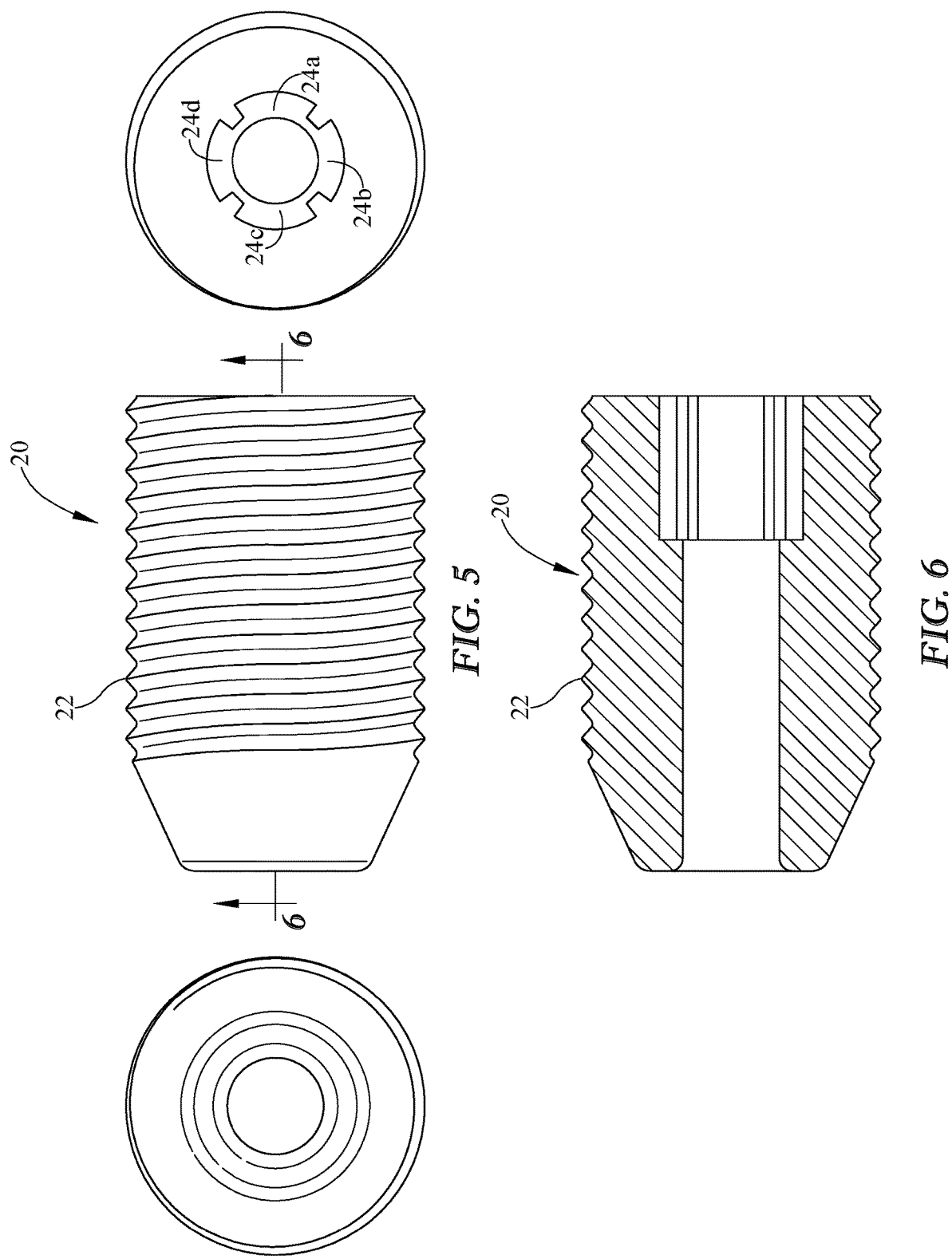

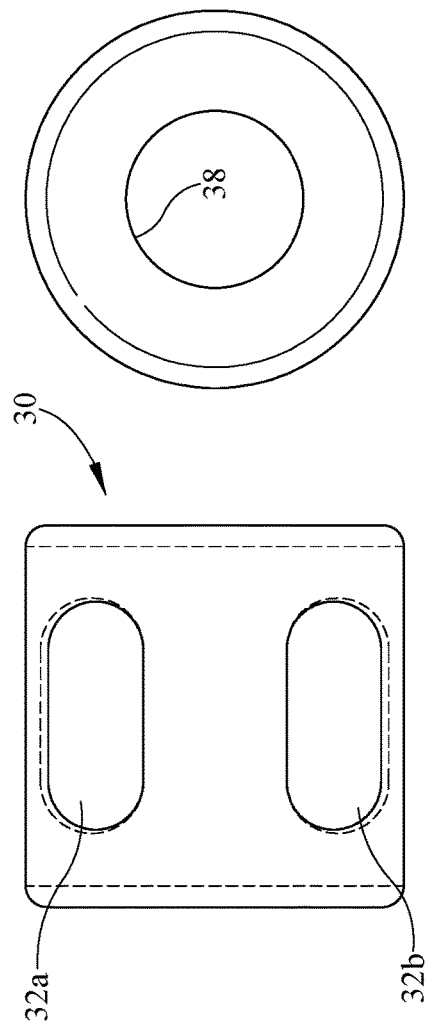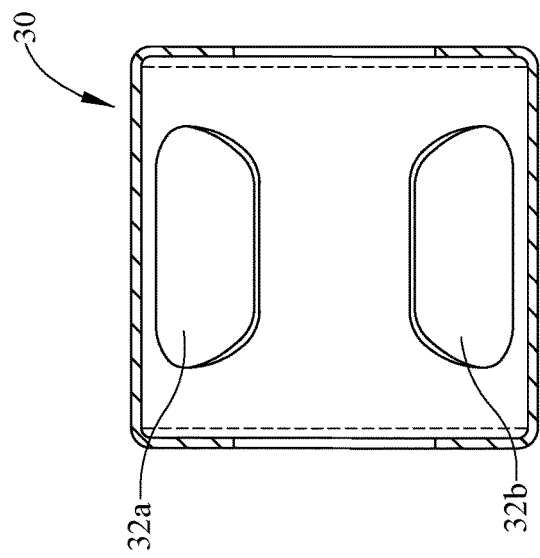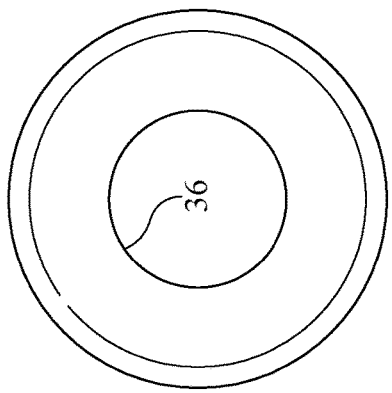

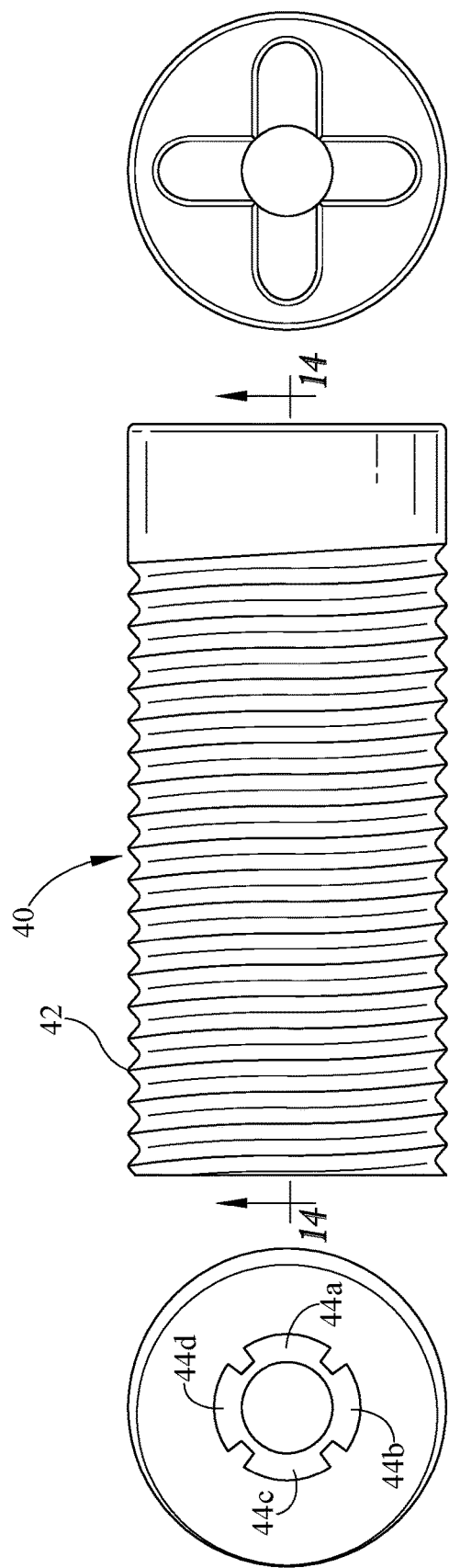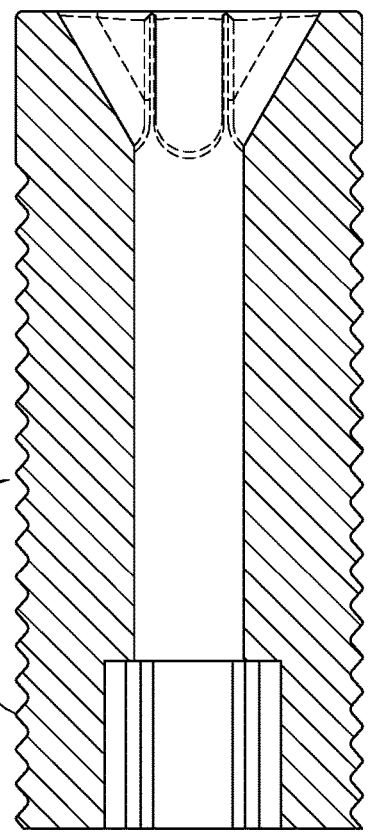
FIG. 13
FIG. 14

KNOTLESS SUTURE ANCHOR

CROSS-REFERENCE TO RELATED APPLICATIONS

This application claims the benefit of U.S. Provisional Application No. 62/618,465, filed Jan. 17, 2018, the disclosures of which are incorporated herein by reference.

FIELD OF DISCLOSURE

The present invention pertains to suture anchors for securing sutures and other filamentary material to soft tissue to reattach the soft tissue to bone.

BACKGROUND

Suture anchors are commonly employed in situations where soft tissue (muscle, tendons or ligaments) becomes detached from bone and must be reattached or secured to bone. The anchor is generally inserted into a preformed hole in the bone, and one or more sutures or similar filamentary material extends from the anchor and is attached to the soft tissue to be secured to the bone. The anchor may be advanced into the bone by rotating the anchor or tapping the anchor into the bone. Knotless suture anchors have been developed for use in arthroscopic surgery. Insertion guides in the general form of elongated tubes having a pointed distal end have also been developed to assist in locating the preformed hole into which the anchor is inserted.

Currently available suture anchors, however, have limitations in their ability to provide sufficient tensioning of the soft tissue while deploying the anchor into the bone, particularly when used in arthroscopic surgery. Additionally, these anchors do not permit easy readjustment or re-tensioning once the anchor has been advanced into the bone. In current designs, the suture or sutures move in conjunction with the anchor as the anchor is advanced into the bone reducing the amount of control over the tensioning of the soft tissue. Similarly, in most current designs, sutures extend throughout the length of the anchor requiring removal of the entire anchor from the bone to readjust the tension and often precluding the use of guides to help locate the preformed hole.

SUMMARY OF THE INVENTION

It is accordingly an object of this invention to produce a knotless suture anchor that permits optimal adjustment of the tension exerted upon the soft tissue while advancing the anchor into the preformed hole in the bone. It is another object of this invention to produce a knotless suture anchor that permits easy readjustment of the tension after the anchor has been advanced into the bone. Lastly, it is an object of this invention to produce a knotless suture anchor that permits use of a guide to facilitate the location of the preformed hole in the bone.

These and other objects of this invention are achieved by the preferred embodiment disclosed herein. This invention is a knotless suture anchor comprising a distal part, an inner tube part, a ring part and a proximal part. The anchor has a center bore that extends longitudinally between a proximal end and a distal end of the anchor. The center bore is configured to receive an insertion guide for engaging the preformed hole in the bone.

The ring part has two pairs of opposing apertures that define first and second suture passageways between an inner surface of the ring part and an outer surface of the inner tube part. One or more sutures may be threaded through the suture passageways. Importantly, the suture passageways do not transverse the center bore. Before or after threading the suture through the suture passageways, the suture can be connected to any suitable tissue to be anchored. The tension exerted on the tissue may be adjusted by pulling the suture through the suture passageways in the ring part. The ring part is configured to move independently of the distal part and proximal part of the anchor. Accordingly, more or less tension may be exerted on the tissue by maneuvering or pulling the suture through the suture passageways in the ring part without interfering with the advancement of the distal part of the anchor into the bone.

When the anchor is fully inserted into the bone, the suture is secured between an outer surface of the anchor and the bone. After insertion of the anchor into the bone, the tension on the tissue may be readjusted by withdrawing the proximal part and ring part of the anchor from the bone, maneuvering the suture in the ring part, and re-advancing the anchor into the bone.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

FIG. 5 shows a side view of the distal part of the suture anchor.

FIG. 6 shows a cross-sectional view of FIG. 5.

FIG. 7 shows a side view of the ring part.

FIG. 8 shows a cross-sectional view of FIG. 7.

FIG. 13 shows a side view of the proximal part.

FIG. 14 shows a cross-sectional view of FIG. 13.

DETAILED DESCRIPTION

Figure 1:
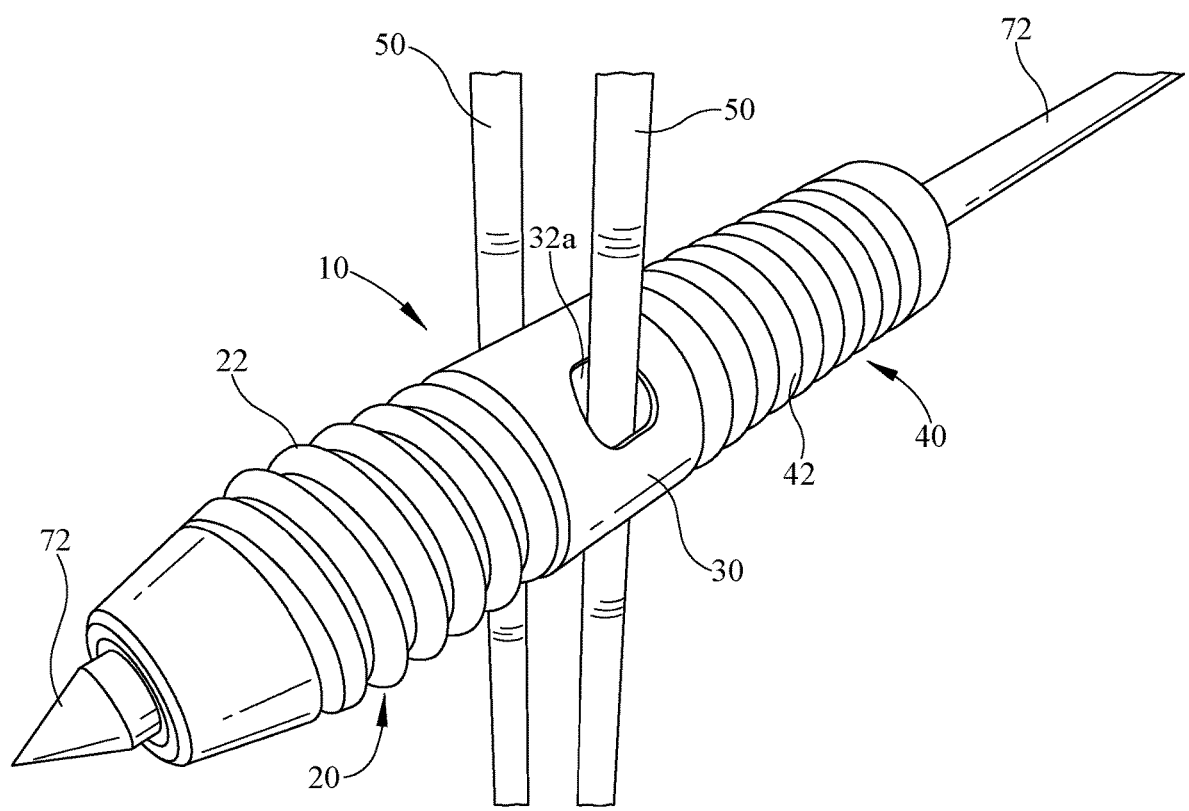
FIG. 1 shows a front perspective view of a knotless suture anchor constructed in accordance with the principles of this invention attached to an insertion guide.

The following description and drawings illustrate embodiments sufficiently to enable those skilled in the art to practice the invention. It is to be understood that the disclosure is not limited to the details of construction and the arrangement of components set forth in the following description or illustrated in the drawings. The invention is capable of other embodiments and of being practiced or of being carried out in various ways. For example, other embodiments may incorporate structural, chronological, process, and other changes. Examples merely typify possible variations. Individual components and functions are optional unless explicitly required, and the sequence of operations may vary. Portions and features of some embodiments may be included in or substituted for those of others. The scope of the application encompasses the appended claims and all available equivalents. The following description is, therefore, not to be taken in a limited sense.

Also, it is to be understood that the phraseology and terminology used herein is for the purpose of description and should not be limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings.

With initial reference to FIG. 1, a knotless suture anchor according to the present teachings is generally illustrated at reference numeral 10. As depicted in FIGS. 1-4, the knotless suture anchor 10 comprises a distal part 20 having an inner and outer surface and a generally cylindrical hollow first inner tubular member having an axial first lumen; a generally cylindrical inner tube part 60 having an inner and outer surface and an axial second lumen; a proximal part 40 having an inner and outer surface and a generally cylindrical hollow second inner tubular member having an axial third lumen; and a ring part 30 having an inner and outer surface and an axial fourth lumen 36.

Figure 3:
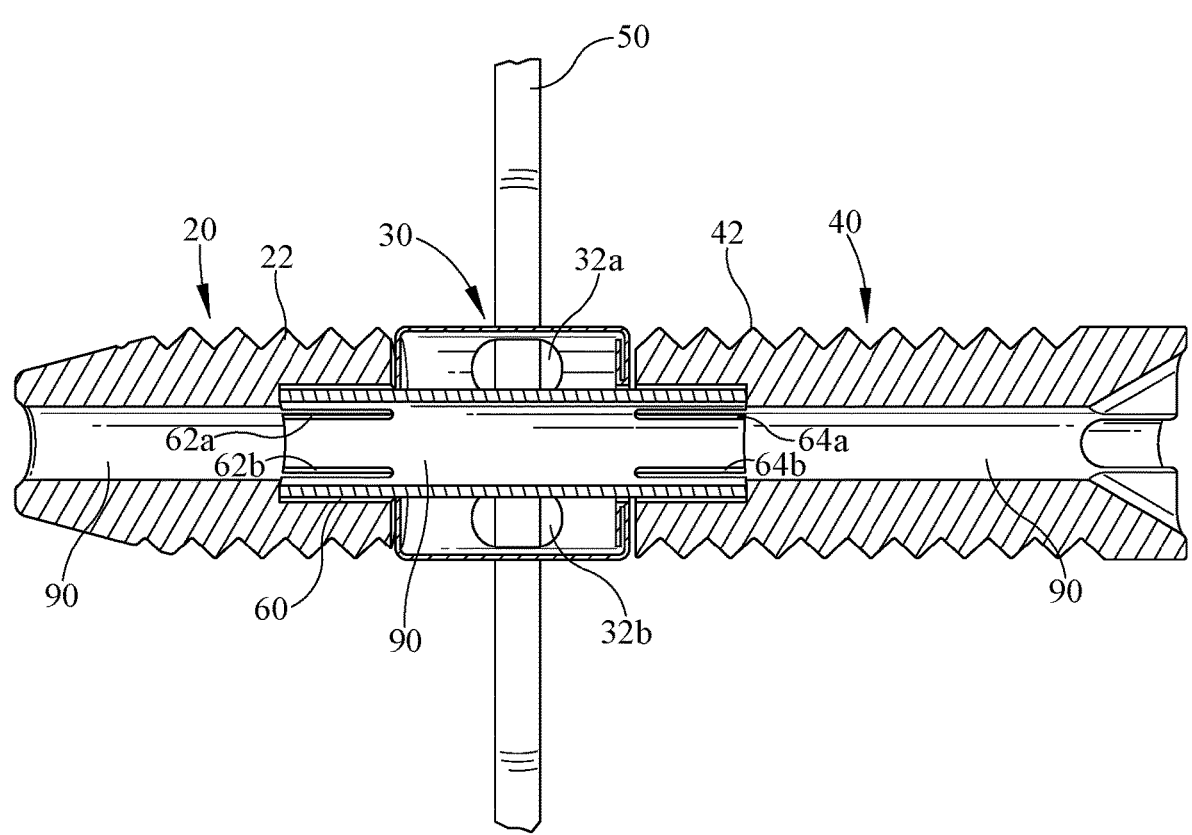
FIG. 3 is a cross-sectional view of the suture anchor.
Figure 4:
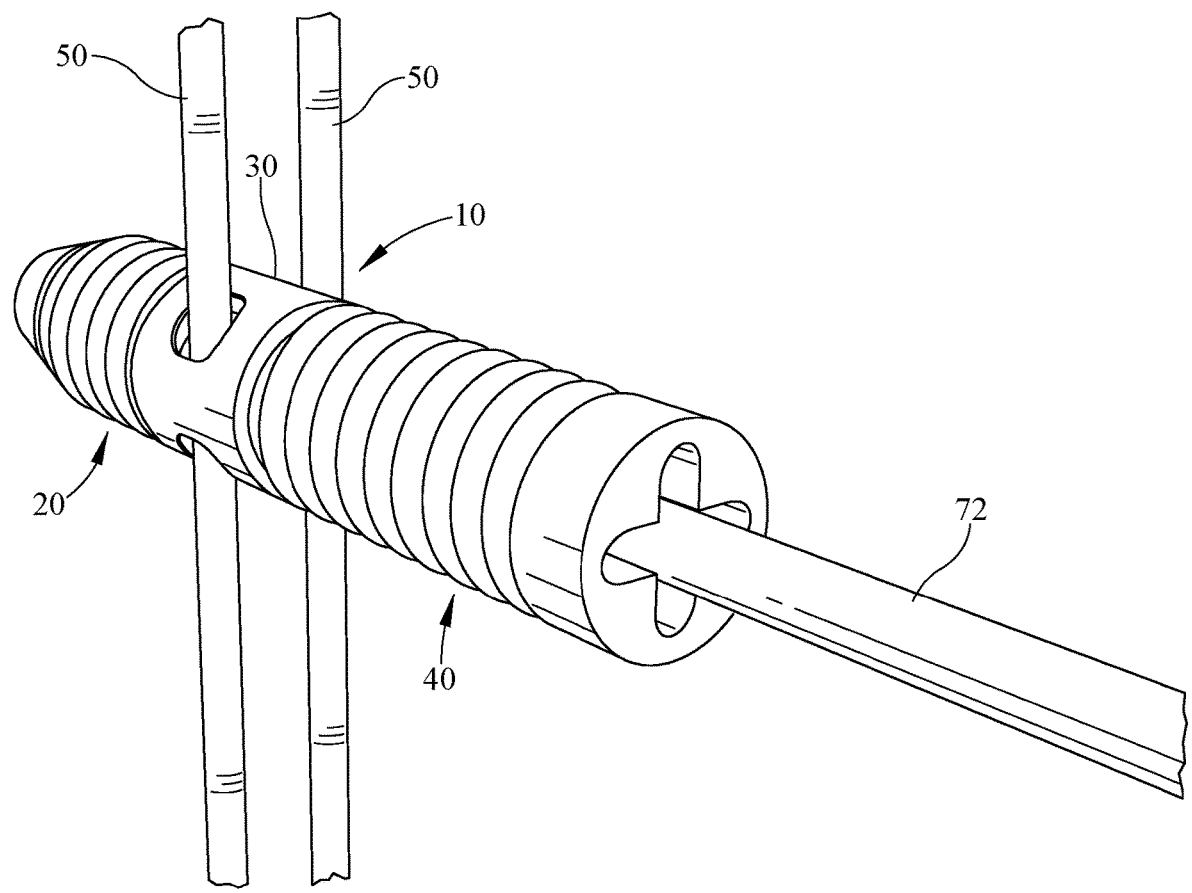
FIG. 4 shows a back perspective view of the knotless suture anchor attached to an insertion guide.
Figure 9:
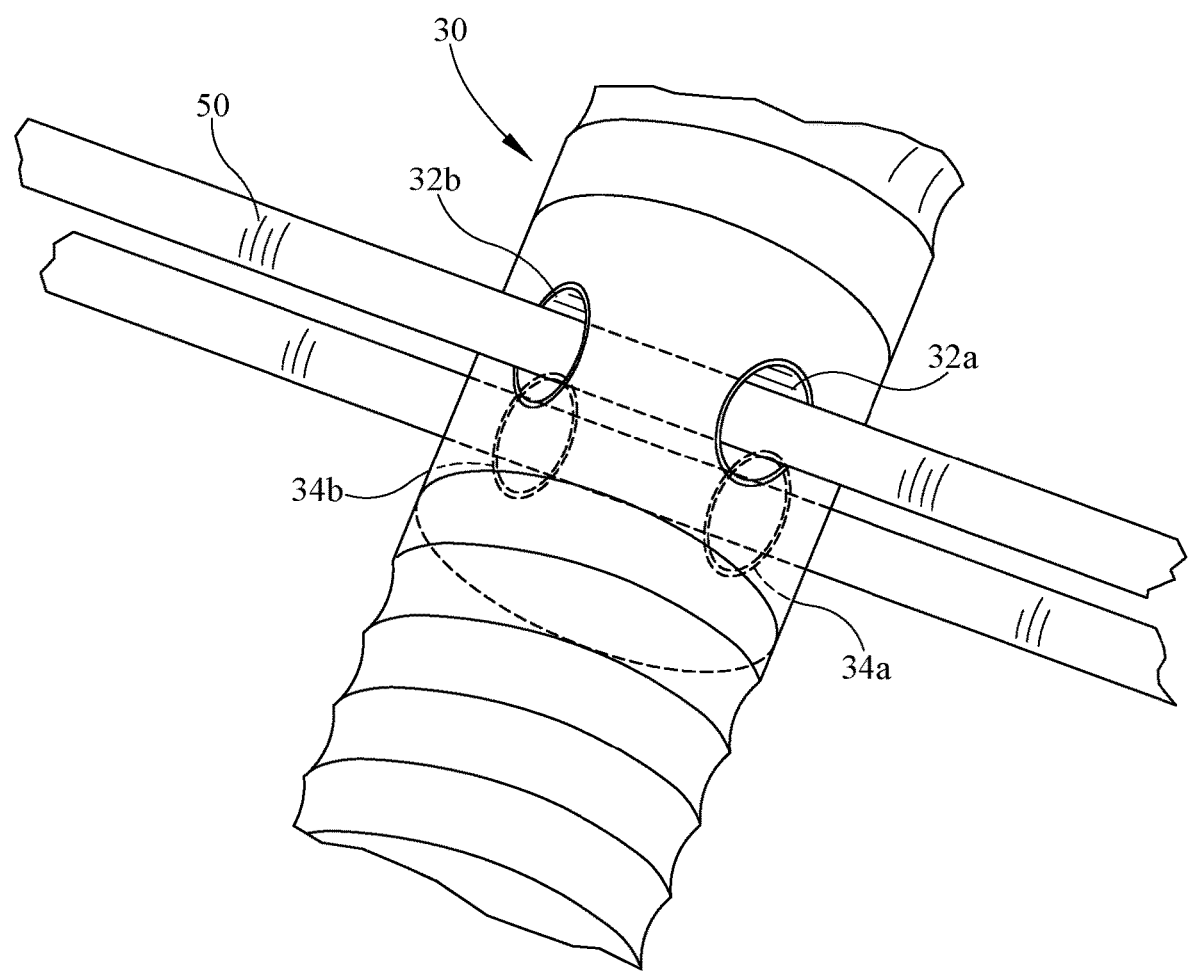
FIG. 9 shows a front perspective view of the ring part.

With reference to FIG. 3, the first, second, and third axial lumens are aligned to define a center bore 90 of the knotless suture anchor 10. The center bore 90 extends longitudinally between a proximal end and a distal end of the suture anchor 10. In some embodiments, the center bore 90 has a diameter of about 1.5 mm. As shown in FIGS. 1 and 4, the center bore 90 is configured to receive an insertion guide 72.

Figure 11:
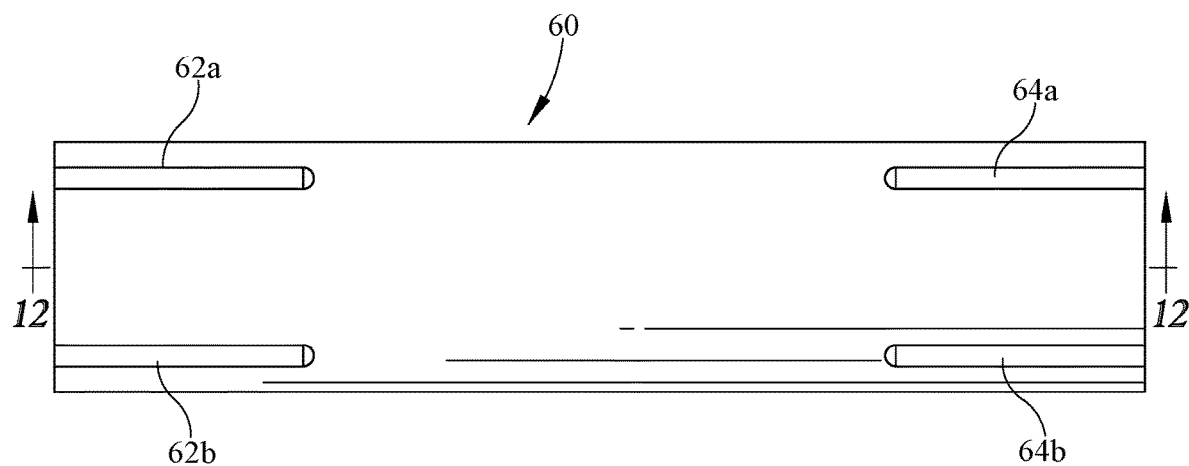
FIG. 11 shows a side view of the inner tube part.
Figure 12:
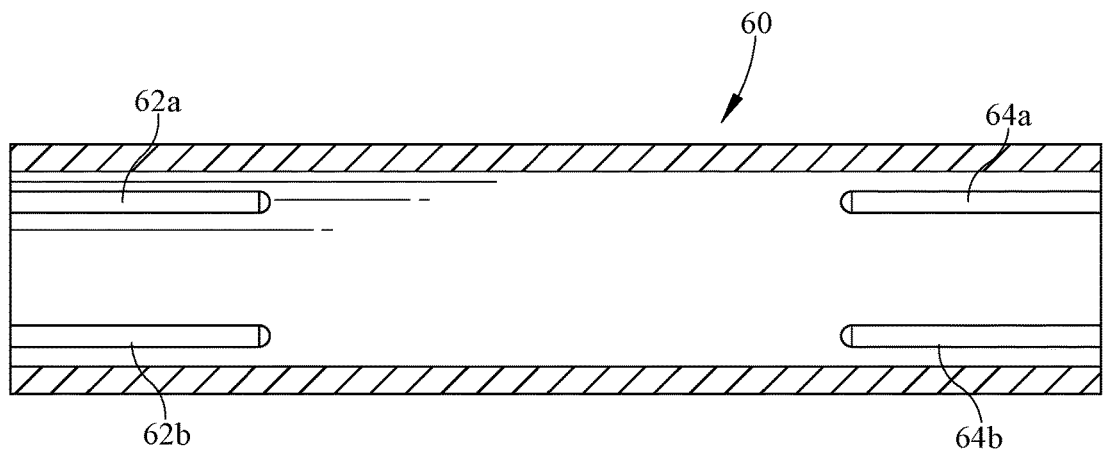
FIG. 12 shows a cross-sectional view of FIG. 11.
Figure 15:
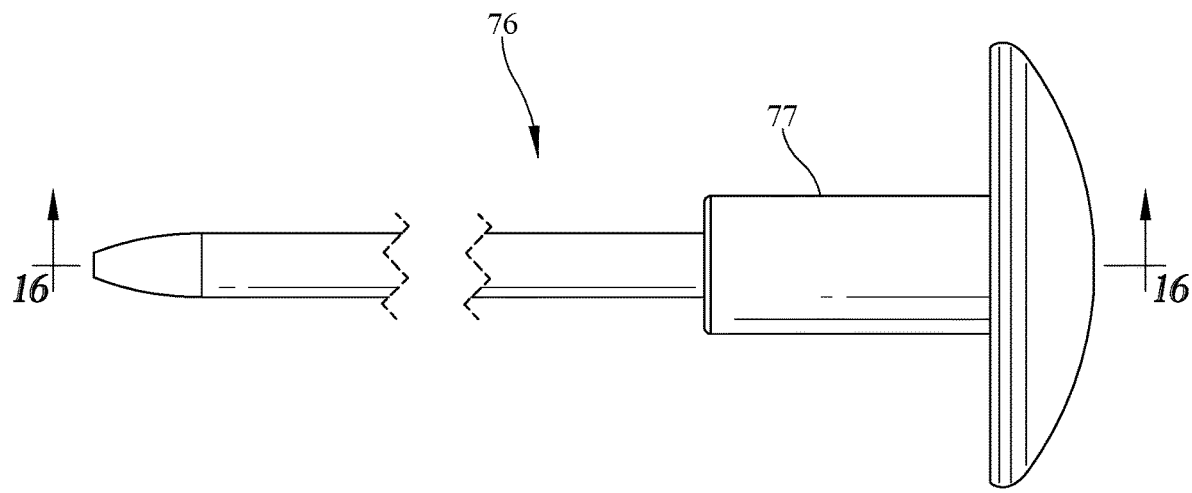
FIG. 15 shows a side view of a cannulated driver for the suture anchor with handle.
Figure 16:
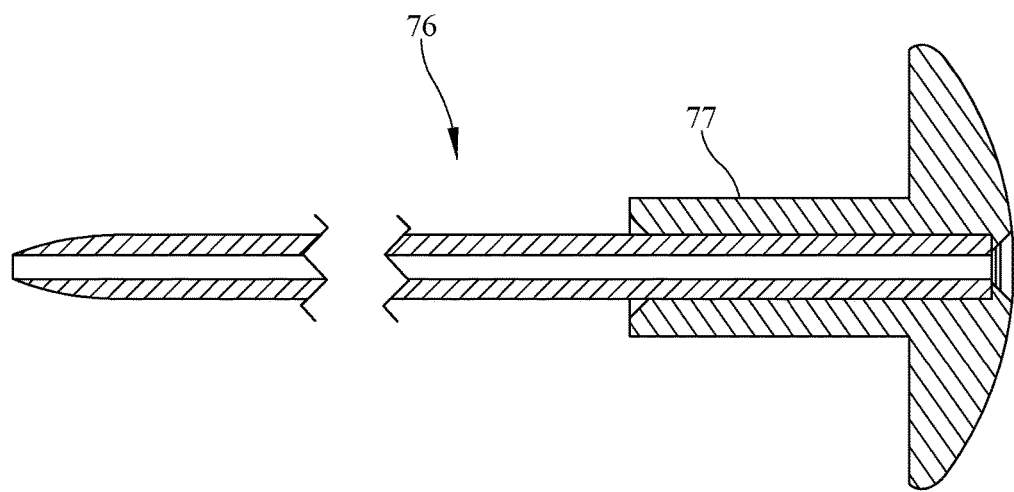
FIG. 16 shows a cross-sectional view of FIG. 15.

The inner tube part 60 is connected to and situated between the distal part 20 and proximal part 40. The inner tube part 60 has a diameter that is bigger than the diameter of the axial second lumen. For example, in some embodiments, the diameter of the inner tube part 60 is about 1.9 mm and the diameter of the axial second lumen is about 1.5 mm. In one embodiment, the inner tube part 60 is connected to the distal and proximal parts 20 and 40 by a system of interlocking grooves and ridges. As depicted in FIG. 6, the diameter of the axial first lumen increases at the proximal end of the distal part 20. In some embodiments, the diameter of the axial first lumen at the proximal end of the distal part 20 is about 1.9 mm. In some embodiments, as depicted in FIG. 5, a first set of four ridges 24a, 24b, 24c and 24d project from the inner surface of the distal part into the axial first lumen at the proximal end of the distal part. As depicted in FIGS. 11 and 12, in one embodiment, the distal end of the inner tube part 60 has a first set of four grooves (for example, two grooves 62a and 62b are shown on FIG. 11) that extend slightly toward the proximal end of the inner tube part 60 and are configured to interlock with the first set of ridges 24a, 24b, 24c and 24d. In such embodiment, the distal end of the inner tube part 60 is connected to the proximal end of the distal part 20 by interlocking the first set of grooves (for example, two grooves of the first set of grooves 62a and 62b are shown on FIGS. 11 and 12) with the first set of ridges 24a, 24b, 24c and 24d.

Similarly, in some embodiments, as depicted in FIGS. 11 and 12, the proximal end of the inner tube part has a second set of four grooves (for example, two grooves of the second set of grooves 64a and 64b are shown on FIGS. 11 and 12) that extend slightly toward the distal end of the inner tube part 60. As depicted in FIG. 14, in some embodiments, the diameter of the axial third lumen increases at the distal end of the proximal part 40. For example, in some embodiments, the diameter of the axial third lumen at the distal end of the proximal part 40 is about 1.9 mm. As depicted in FIG. 13, in some embodiments, a second set of four ridges 44a, 44b, 44c, and 44d project from the inner surface of the proximal part 40 into the axial third lumen at the distal end of the proximal part 40. In such embodiments, the second set of grooves (for example, two grooves of the second set of grooves 64a and 64b are shown in FIGS. 11 and 12) on the inner tube part 60 are configured to interlock with the second set of ridges 44a, 44b, 44c, and 44d extending into the third axial lumen. The system of grooves and ridges described herein represent one method by which the inner tube part may be connected with the distal and proximal parts. The size of the grooves and ridges may be adjusted to create a tighter or looser fit as preferred. Those skilled in the art will recognize and appreciate other connectors and methods for connecting the inner tube part 60 to the distal and proximal parts 20 and 40.

Figure 2:
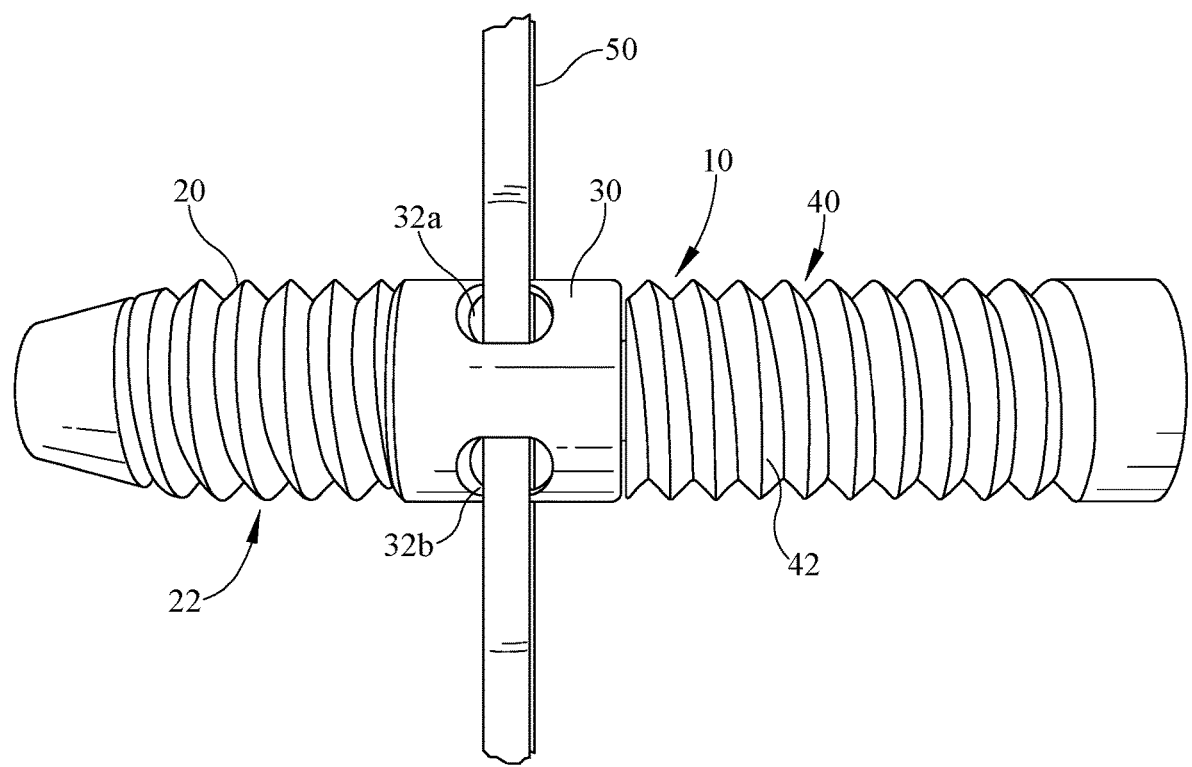
FIG. 2 shows a side view of the knotless suture anchor.

As depicted in FIGS. 1 and 2, the outer surfaces of the distal part 20, ring part 30, and proximal part 40 define an outer surface of the suture anchor 10 having a proximal end and a distal end. The length of the suture anchor is preferably in the range of 20-24 mm. With additional references to FIGS. 5-6 and 13-14, the outer surfaces of the distal part 20 and proximal part 40 may have radially outwardly extending projections 22 and 42 to engage the wall of the preformed bone hole as the anchor is advanced into the bone.

Figure 17:
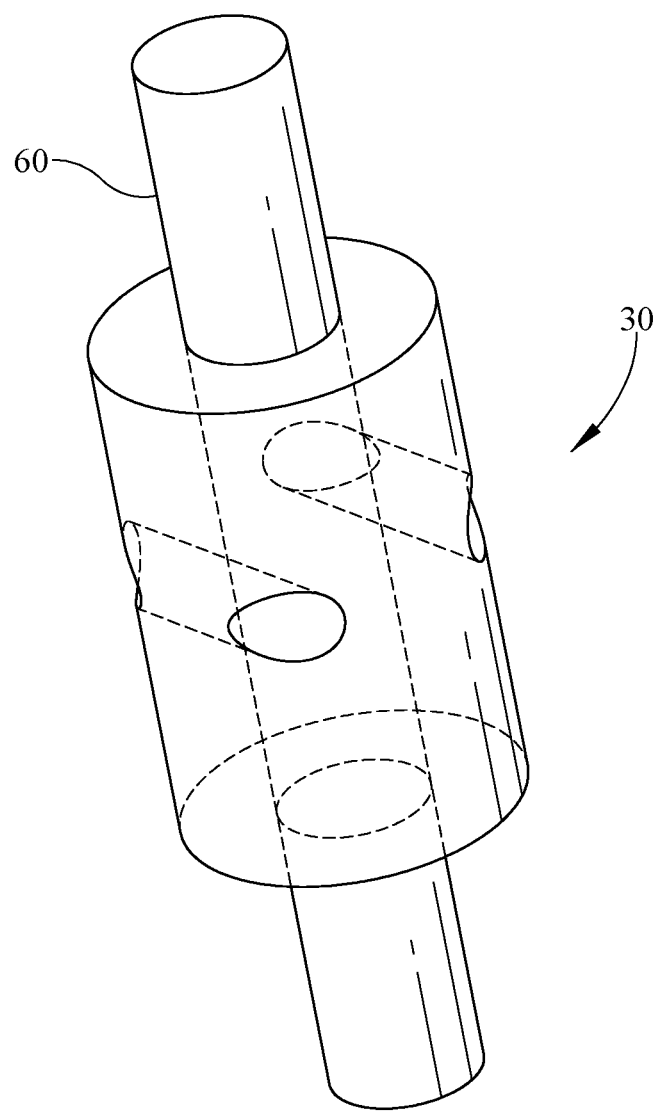
FIG. 17 shows a schematic view of the ring part and inner tube part.
Figure 18:
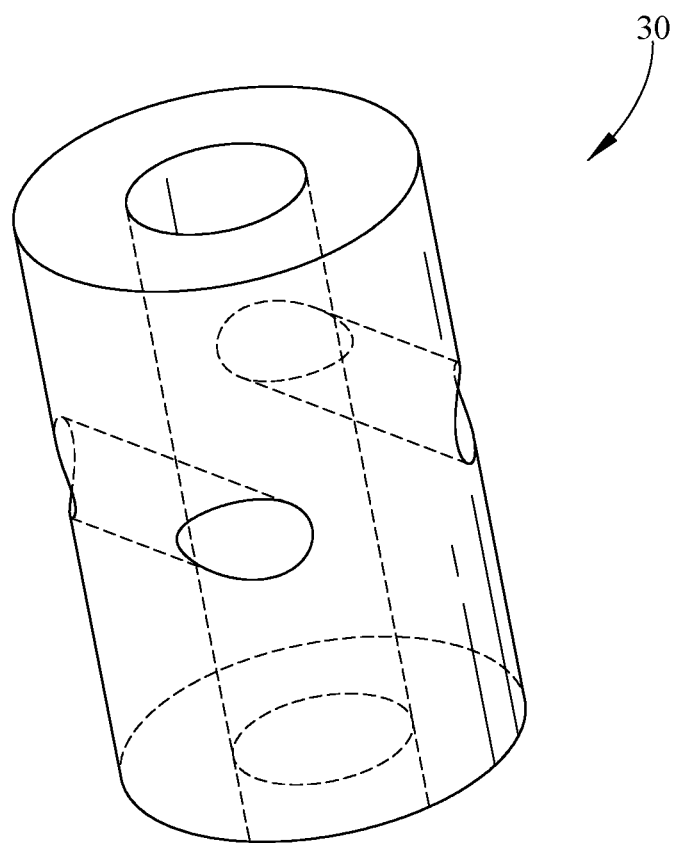
FIG. 18 shows a schematic view of the ring part.
Figure 19:
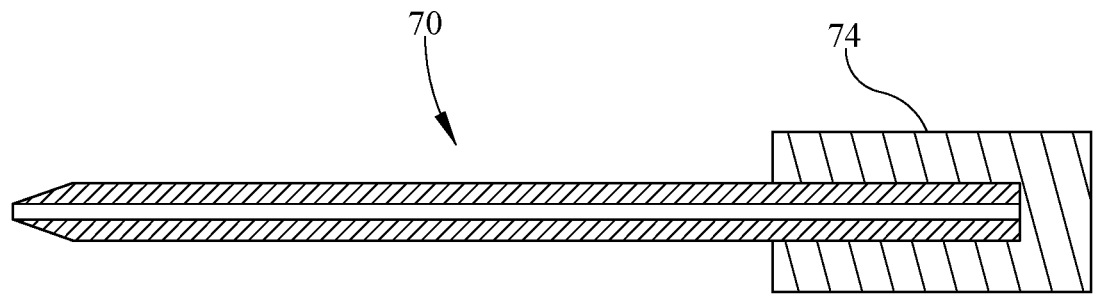
FIG. 19 shows a side view of a cannulated punch and handle.
Figure 20:
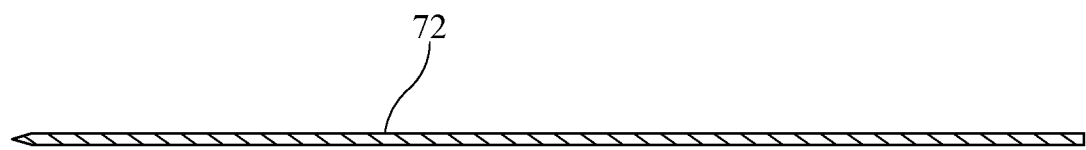
FIG. 20 shows a side view of an insertion guide.
Figure 21:
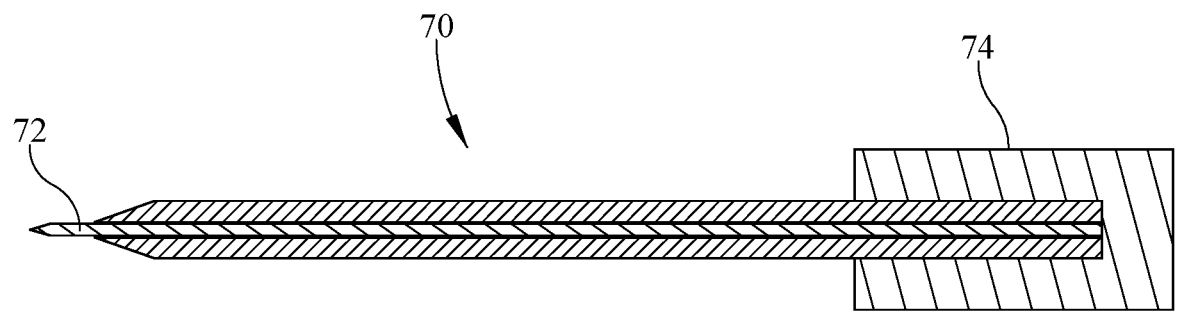
FIG. 21 shows a side view of a cannulated punch, insertion guide, and handle.

Features of the ring part 30 will now be described. The ring part 30 has a generally smooth inner and outer surface. The ring part is generally hollow. The ring part 30 has a distal end and a proximal end. The distal end of the ring part 30 is aligned with a proximal end of the distal part 20. In some embodiments, the distal end of the ring part 30 has a diameter of approximately 4.5 mm. As depicted in FIGS. 7, 17, and 18 the distal end of the ring part 30 is configured to receive the inner tube part 60. In some embodiments, as depicted in FIGS. 7 and 17, the distal end of the ring part 30 has an opening 36 for receiving the inner tube part 60. In some embodiments, the opening 36 on the distal end of the ring part 30 for receiving the inner tube part 60 is approximately 2 mm in diameter.

The proximal end of the ring part 30 is aligned with a distal end of the proximal part 40. In some embodiments, the proximal end of the ring part 30 has a diameter of approximately 4.5 mm. As depicted in FIGS. 7, 17, and 18, the proximal end of the ring part 30 is configured to receive the inner tube part 60. In some embodiments, the proximal end of the ring part 30 has an opening 38 for receiving the inner tube part 60. In some embodiments, the opening 38 for receiving the inner tube part 60 is approximately 2 mm in diameter.

As depicted in FIGS. 17-18, the ring part 30 is generally hollow and has an axial fourth lumen. The diameter of the ring part is larger than the diameter of the axial fourth lumen. In some embodiments, the diameter of the ring part is about 4.9 mm and the diameter of the axial fourth lumen is about 4.5 mm. As depicted in FIGS. 3 and 17 the diameter of the axial fourth lumen of the ring part is larger than the diameter of the inner tube part 60. The inner tube part 60 is situated inside the axial fourth lumen of the ring part, but the ring part 30 is not attached or affixed to the inner tube part 60. This design permits the inner surface of the ring part 30 to come into contact with the outer surface of the inner tube part 60, but, importantly, the ring part 30 does not stick or adhere to the inner tube part 60. In some embodiments, the diameter of the axial fourth lumen of the ring part is about 4.5 mm, and the diameter of the inner tube part 60 is about 1.9 mm. Accordingly, in such embodiments, the space or gap between the outer surface of the inner tube part and the inner surface of the ring part is about 1.25 mm.

As depicted in FIG. 2, in some embodiments, the ring part 30 is situated between the distal part 20 and proximal part 40 but is not connected to the distal and proximal parts 20 and 40 via any form of connectors, attachments, or adhesives. Rather, the ring part 30 remains situated between the distal part 20 and proximal part 40 in a relatively stationary position as a result of the placement of the inner tube part 60 inside the ring part 40 and the location of the distal and proximal parts 20 and 40 above and below the ring part 30. For example, in some embodiments, the diameters of the proximal end of the distal part 20 and the distal end of the proximal part 40 are larger than the diameter of the ring part 30, so that the distal part 20 and proximal part 40 restrict any longitudinal movement of the ring part 30. For example, in some embodiments, the diameter of the ring part 30 is about 4.9 mm; and the diameters of the proximal end of the distal part 20 and distal end of the proximal part 40 are each about 5 mm. In some embodiments, the distance between the distal and proximal parts 20 and 40 having the inner tube part 60 attached is about 4 mm. In such embodiments, the length of the ring part is about 3.9 mm.

Turning to FIGS. 7-10, the ring part 30 further comprises a first pair of opposing apertures 32a and 32b and a second pair of opposing apertures 34a and 34b for receiving a suture 50. The first pair of apertures 32a and 32b generally defines a first suture passageway between the inner surface of the ring part 30 and the outer surface of the inner tube part 60. The second pair of apertures 34a and 34b generally defines a second suture passageway between the inner surface of the ring part 30 and outer surface of the inner tube part 60. The space between the inner surface of the ring part 30 and outer surface of the inner tube part 60 is generally free of obstructions. For purposes of clarity, the first and second suture passageways do not traverse the center bore 90. The first and second suture passageways are spaced apart and are arranged generally parallel to one another.

Figure 10:
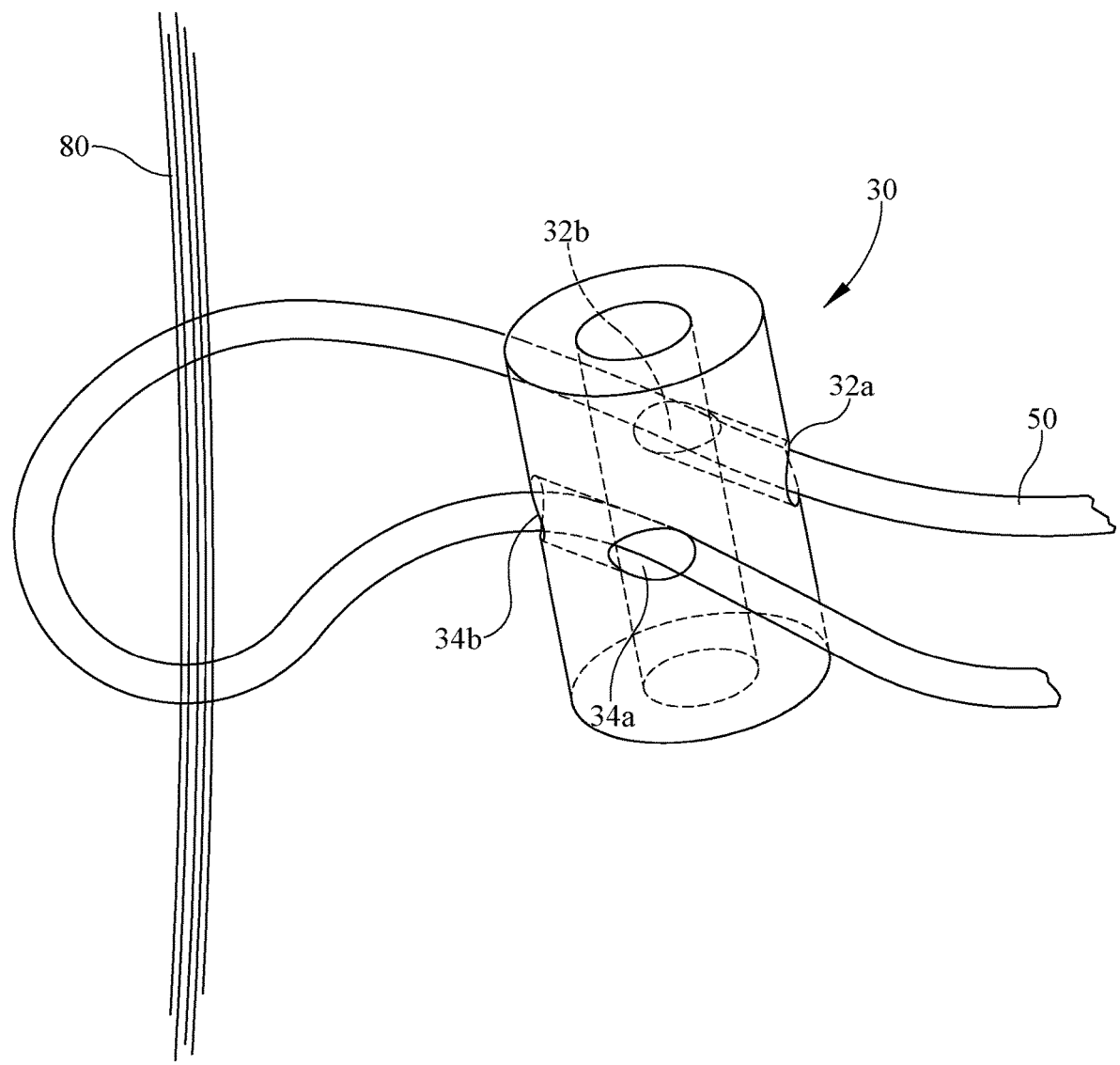
FIG. 10 shows a schematic view of the ring part with a suture attached to soft tissue.

Each aperture 32a, 32b, 34a and 34b has a diameter larger than that of the suture 50 permitting the suture 50 to be maneuvered through the apertures 32a, 32b, 34a and 34b. The suture 50 is threaded generally transversally through the first suture passageway and generally transversally through the second suture passageway. As shown in FIG. 10, before or after threading the suture 50 through the apertures 32a, 32b, 34a and 34b, the suture may be connected to any suitable tissue 80 to be anchored. Tension on the tissue 80 may be adjusted by pulling or maneuvering the suture 50 through the suture passageways in the ring part 30.

The suture anchor 10 may be advanced into a preformed hole in bone 100 until the distal part 20 is inside the bone 100 at which time the tension on the tissue 80 may be adjusted by maneuvering or pulling on the suture 50. Once the desired tension is achieved, the ring part 60 and proximal part 40 may be advanced into the bone wherein the suture 50 will be compressed between the outer surface of the suture anchor 10 and bone 100. The tension on the tissue 80 may be readjusted by withdrawing only the proximal part 40 and ring part 30 from the bone 100, maneuvering the suture 50 in the ring part 30, and re-advancing the proximal part 40 and ring part 30 into the bone. This design permits easy readjustment of the tension on the suture 50 without requiring the anchor 10 to be completely removed from the bone 100.

The suture anchor can be made of any suitable biocompatible material such as a suitable metallic or polymer. Changes in the various dimensions provided herein may be made depending upon the composition, type and size of suture to be used. Various modifications and alterations of this invention will be apparent to those skilled in the art without departing from the scope of this invention. It should be understood that the invention is not limited to the preferred embodiments disclosed herein.

As depicted in FIGS. 1 and 4, in some embodiments, the center bore 90 of suture anchor 10 is configured to receive an insertion guide 72, which may be used to facilitate implantation of the suture anchor 10 into bone 100. As shown in FIGS. 19-24, in some embodiments, the insertion guide 72 is advanced into bone using a cannulated punch 70. In some embodiments, the punch 70 is a tube of metal having a handle 74 at its proximal end. The cannulated punch 70 is used for housing and maneuvering the insertion guide 72.

In a preferred embodiment, as depicted in FIGS. 15, 16, 25 and 26, a cannulated anchor driver 76 can be used to drive the anchor 10 into the bone 100. The cannulated anchor driver 76 is a tube of metal having a lumen for harboring the insertion guide 72, and a handle 77. In some embodiments, the cannulated anchor driver 76 may have a cross shape or hexagonal shape tip at its distal end. In some embodiments, the lumen of the cannulated anchor driver 76 may have a diameter of about 1.5 mm, and the insertion guide 72 may have a diameter of about 1.4 mm.

Figure 22:
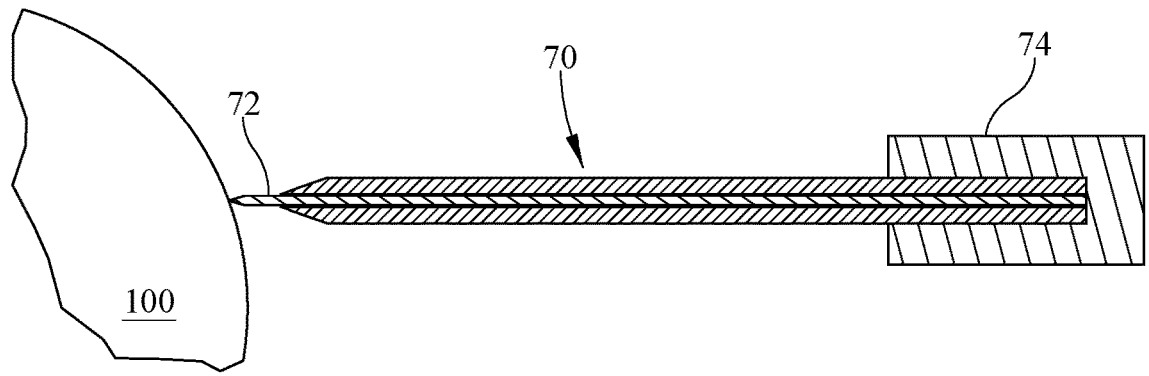
FIG. 22 shows a side view of a cannulated punch with an insertion guide adjacent to bone.
Figure 23:
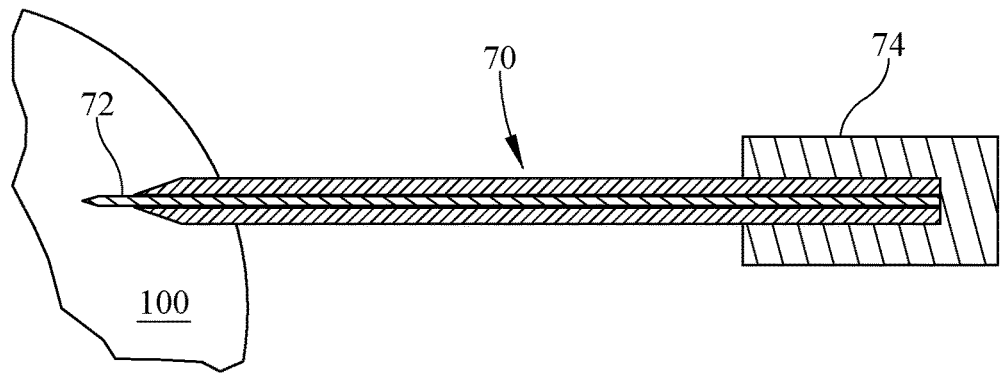
FIG. 23 shows a side view of the deployment of an insertion guide into bone utilizing a cannulated punch.
Figure 24:
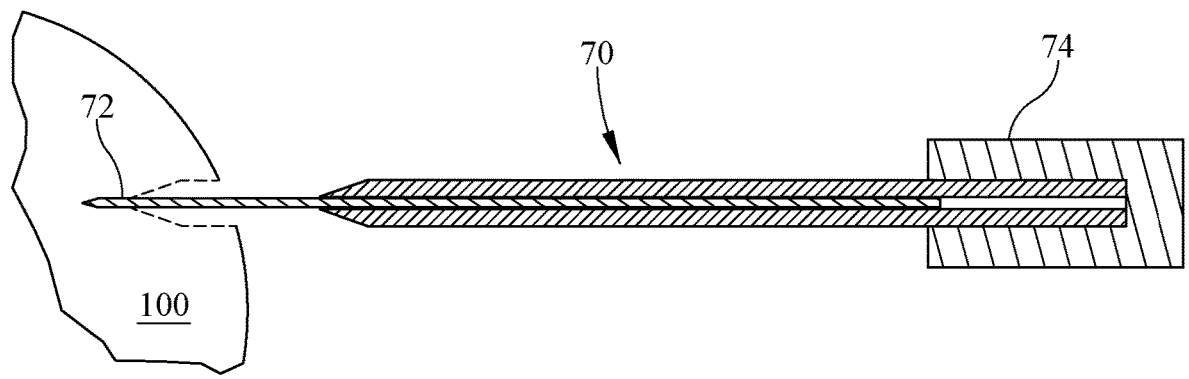
FIG. 24 shows a side view of the deployment of an insertion guide into bone utilizing a cannulated punch.
Figure 25:
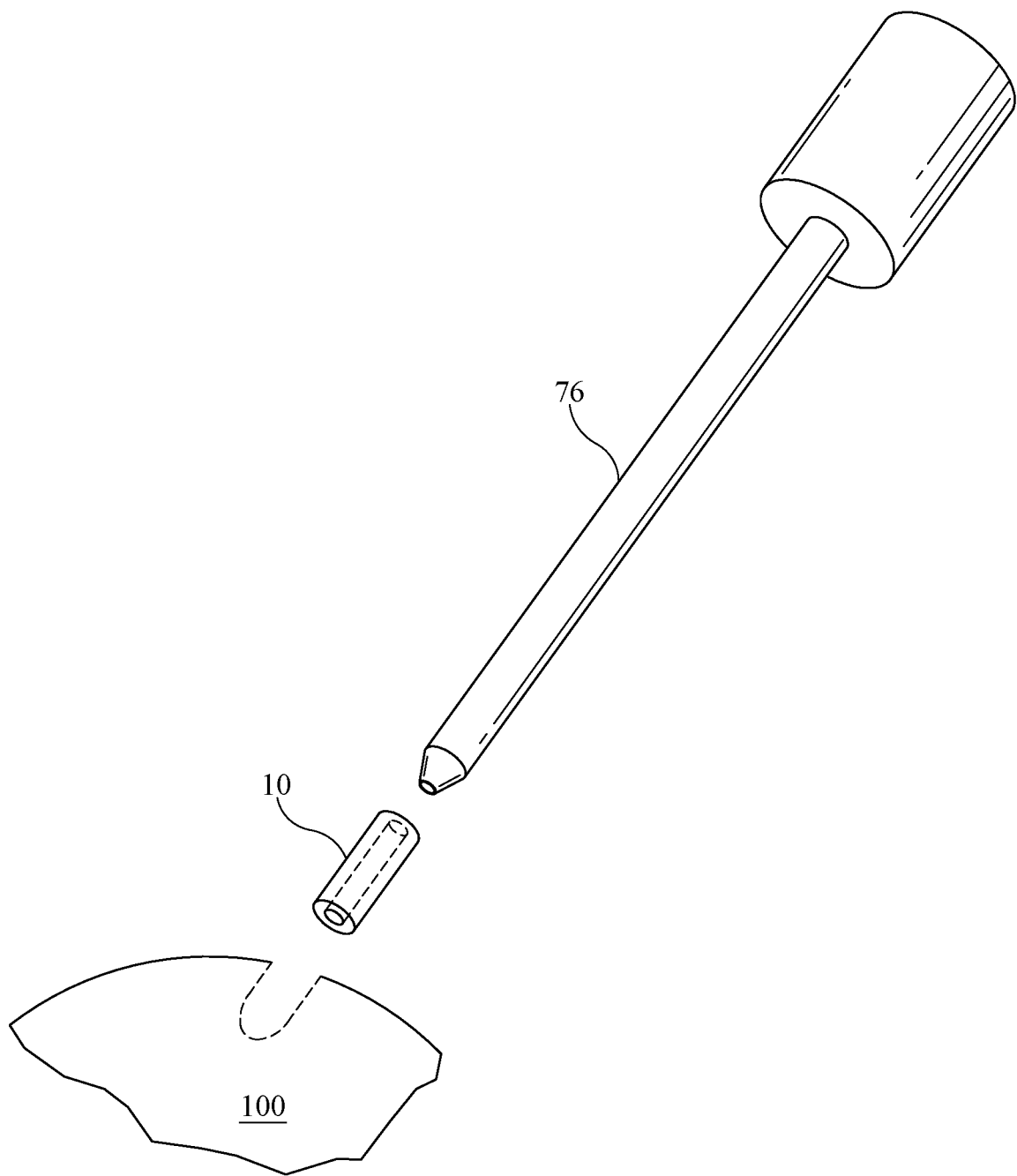
FIG. 25 shows a schematic view of a cannulated anchor driver, suture anchor and bone.
Figure 26:
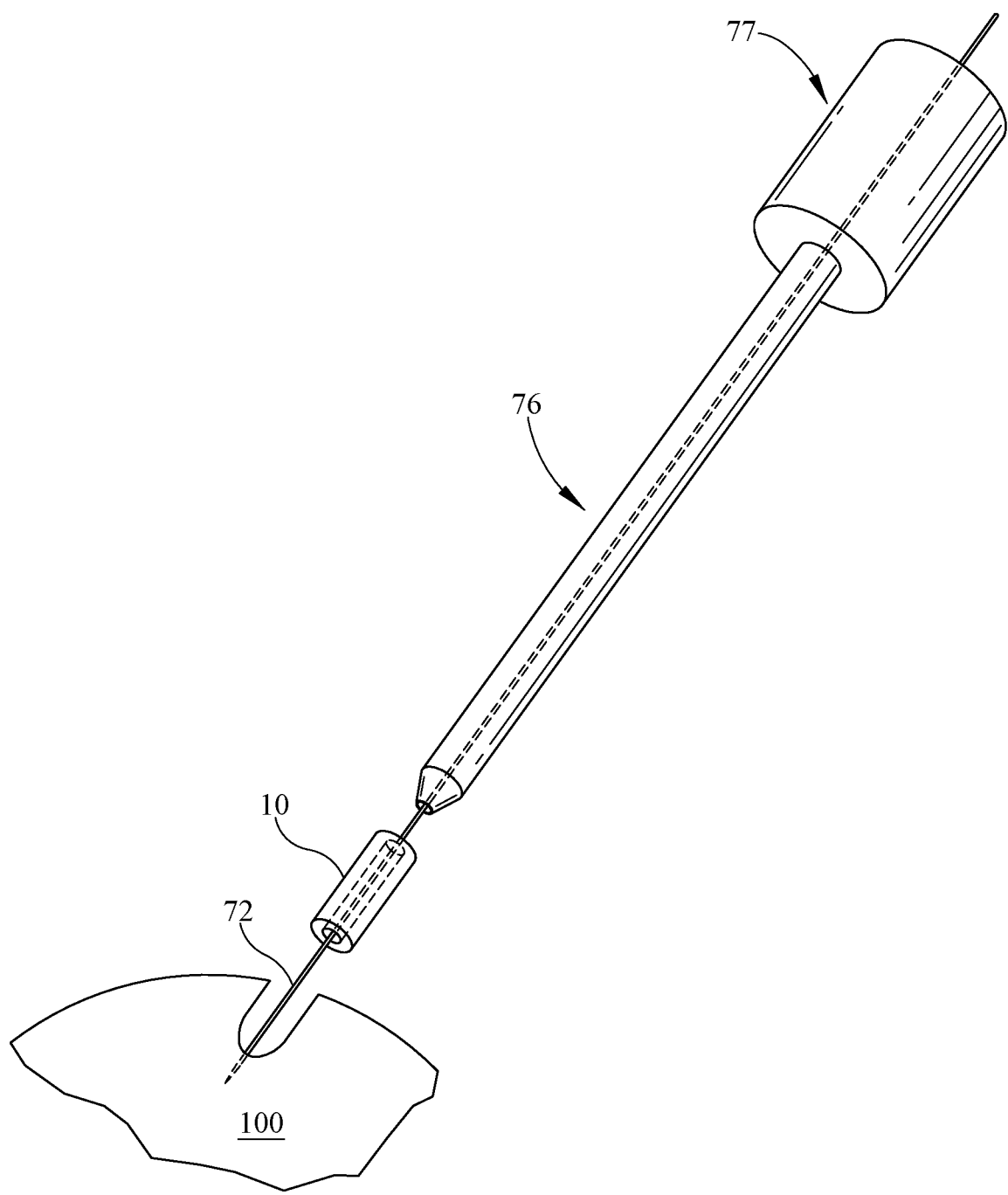
FIG. 26 shows a schematic view of a cannulated anchor driver, suture anchor, insertion guide, and bone.

In some embodiments, as depicted in FIGS. 22-24, a cannulated punch 70 having a cannulated anchor driver 76 may be used to advance the insertion guide 72 into the bone 100 forming a hole in the bone 100. After deployment of the insertion guide 72 into the bone 100, the punch 70 may be removed while the insertion guide 72 remains in the bone 100. The suture anchor 10 and the cannulated driver 76 may then be placed on top of the insertion guide 72 through the center bore 90 and advanced into bone 100 with the cannulated driver 76.

The foregoing description of the embodiments has been provided for purposes of illustration and description. It is not intended to be exhaustive or to limit the disclosure.

What is claimed is:

1. A suture anchor assembly comprising:
   a suture;
   a suture anchor comprising:
      a distal part having a distal end, a proximal end, and a generally cylindrical hollow inner tubular member having an axial first lumen;
      a generally cylindrical inner tube part having a distal end, a proximal end, and an axial second lumen;
      a proximal part having a distal end, a proximal end, and a generally cylindrical hollow inner tubular member having an axial third lumen;
      a center bore defined by the axial first, second and third lumens;
      a ring part situated between the distal and proximal parts, wherein the ring part is configured to move independently relative to the distal part and the proximal part and further comprises a first and second pair of opposing apertures for receiving the suture and
      wherein the suture is directed along a first suture passageway defined by the first pair of opposing apertures and a second suture passageway defined by the second pair of opposing apertures and wherein the suture passageways do not transverse the center bore;
   radially outwardly extending projections on an outer surface of the distal part and on an outer surface of said proximal part for engaging bone;
   wherein said ring part further comprises an axial fourth lumen having a diameter larger than the diameter of the inner tube part;
   wherein said inner tube part is situated inside said axial fourth lumen;
   wherein said ring part is not attached to said distal part or said proximal part; and
   wherein longitudinal movement of said ring part is restricted by said distal part and said proximal part.

2. A suture anchor assembly according to claim 1, wherein said distal part further comprises a first set of ridges extending from an inner surface of said distal part into the axial first lumen and said inner tube part further comprises a first set of grooves configured to interlock with said first set of ridges.

3. A suture anchor assembly according to claim 2, wherein said proximal part further comprises a second set of ridges extending from an inner surface of said proximal part into the axial third lumen and said inner tube part further comprises a second set of grooves configured to interlock with said second set of ridges.

4. A suture anchor assembly according to claim 1, wherein the diameter of said proximal end of said distal part is larger than the diameter of the ring part.

5. A suture anchor assembly according to claim 4, wherein the diameter of said distal end of said proximal part is larger than the diameter of the ring part.

6. A suture anchor assembly according to claim 1, further comprising a cannulated punch and an insertion guide for forming a hole in bone.

7. A suture anchor assembly according to claim 6, wherein the center bore is configured to receive the insertion guide for engaging bone.

8. A suture anchor assembly according to claim 6, wherein the punch further comprises a handle.

9. A suture anchor assembly according to claim 6 further comprising a cannulated anchor driver for advancing the suture anchor into bone.

10. A suture anchor assembly according to claim 9 wherein the cannulated anchor driver comprises an axial fifth lumen for housing the insertion guide.

* * * * *